United States Patent [19]

Hohlweck et al.

[11] Patent Number: 4,635,198
[45] Date of Patent: Jan. 6, 1987

[54] APPARATUS FOR MEASURING CROSS-SECTIONS ON OBJECTS, MORE ESPECIALLY ON PARTS OF THE BODY

[75] Inventors: Hans Hohlweck, Bonn; Gernold Plath, Hennef; Friedhelm Baisch, Neunkirchen-Seelscheid, all of Fed. Rep. of Germany

[73] Assignee: Deutsche Forschungs-und Versuchsanstalt für Luft-und Raum-fahrt e.V., Fed. Rep. of Germany

[21] Appl. No.: 639,017

[22] Filed: Aug. 9, 1984

[30] Foreign Application Priority Data

Aug. 12, 1983 [DE] Fed. Rep. of Germany ....... 3329134

[51] Int. Cl.⁴ ...................... G06F 15/42; G01B 17/00
[52] U.S. Cl. .................................. 364/414; 364/564; 310/334; 367/140; 73/628; 73/632
[58] Field of Search .......... 73/528, 518, 590, 632–640, 73/628, DIG. 4; 364/414, 560–564; 310/334–337; 367/140

[56] References Cited

U.S. PATENT DOCUMENTS

| | | | |
|---|---|---|---|
| 4,229,978 | 10/1980 | Sholl | 73/632 |
| 4,357,690 | 11/1982 | Kuroda | 73/632 |
| 4,409,838 | 10/1983 | Schomberg | 73/602 |
| 4,437,332 | 3/1984 | Pittaro | 73/644 X |

FOREIGN PATENT DOCUMENTS 0111710 7/1983 Japan ..................................... 73/632

OTHER PUBLICATIONS

J. Johansson et al., "Computer–Controlled Laser Beams in Object Dimension Measurements", *Optical Engineering*, vol. 18, No. 4, Jul.-Aug. 1979, pp. 384–386.

*Primary Examiner*—Jerry Smith
*Assistant Examiner*—G. Hayes
*Attorney, Agent, or Firm*—Diller, Ramik & Wight

[57] ABSTRACT

Sound heads (SK1 to SK3) are fixed, distributed peripherally, on the part of the body, e.g. an arm or leg. Each of the sound heads is able to transmit ultrasonic signals along a measuring section (MS1 to MS3) leading to another sound head, which signals are received by the other sound head. The sound heads can consist of angularly arranged sound members (14). In this way, all three sides of a polygon formed by the sound heads are measured, from which measurements the surface area of the polygon can be determined.

35 Claims, 4 Drawing Figures

APPARATUS FOR MEASURING CROSS-SECTIONS ON OBJECTS, MORE ESPECIALLY ON PARTS OF THE BODY

SUMMARY OF THE INVENTION

The invention relates to an apparatus for measuring cross-sections on objects, more especially on parts of the body, comprising at least three sound heads which are to be arranged distributed around the periphery of the part of the body and which contain oscillator elements for transmitting and receiving ultrasonic waves and which, in pairs, form distance-measuring means for the measurement of side lengths of the polygon formed by the measuring heads, and comprising a calculating or computing means for determining the surface or area content of the polygon and/or of the part of the body.

BACKGROUND OF THE INVENTION

It is known to arrange sound heads on the human body in order to carry out length measurements (Aviation, Space and Environmental Medicine, April 1982, pages 375 to 378, and May 1983, pages 458 to 463). In such an arrangement, one of the sound heads is energised electrically with an ultrasonic frequency, so that it emits ultrasonic signals, which are received by the other sound head. The spacing of the two sound heads is determined from the transmission time difference between emission and reception. The term "sound" is to cover generally all vibrations which are propagated by molecule movement in a medium, i.e. also ultrasonic waves.

It order to determine the cross-section of limbs or extremities of the human body, it is known to arrange three sound heads around the corresponding extremity, for example, the lower leg. Two of the sound heads have a relatively small spacing, which is assumed to be known. At the time of measurement, it is presupposed that these two sound heads, disposed relatively close to one another, have a prescribed constant spacing from one another, which is known and forms the basis in connection with the calculation of the area content of the triangle formed between the sound heads. The calculation of the other legs of the triangle is effected by emitting ultrasonic waves from that sound head which is opposite the short side of the triangle. The two other sound heads receive these signals. In this way, with the aid of two measurement distances and one side length of the triangle, which is assumed to be already known, the area content of the triangle is determined by calculation. This known apparatus has the disadvantage that the short side length of the triangle, which is assumed to be constant, is in actual fact not constant. On the contrary, it is the peripheral segment of the band length between the two sound heads which is constant, but not the shortest distance between these latter. It is an additional disadvantage with the known arrangement that two of the sound heads have to be disposed relatively close to one another, the consequence of which is that the triangle formed by the sound heads is, as a rule, an obtuse-angled triangle, which fills only a very small portion of the cross-sectional area of the part of the body to be measured. The measurment is therefore relatively inaccurate.

OBJECTS OF THE INVENTION

The invention has for its object to provide an apparatus of the type as previously referred to, which enables an exact measurement of the side lengths of the polygon to be made.

A first solution of this problem consists, according to the invention, in that the sound heads are designed for the transmission and the reception of ultrasonic waves, that the oscillator members consist of angular plates, of which both legs with their oscillating surface respectively face a leg of the oscillator member of another sound head, and that a switching means is provided, which switches over at least two sound heads between transmission and reception in such a way that all measurement distances formed between the sound heads are measured.

The basic principle of the invention consists in that the length of each of the measurement distances which are formed between the sound heads are measured. However, this general principle is not able to be readily carried into effect, because ultrasonic waves are emitted with a certain directional effect. A piezoelectric oscillator member, which is energised with an electric voltage, emits a directional characteristic consisting of several "legs" with respect to the oscillating surface. This means that each oscillator body is able to transmit mainly in only one direction, so that its signals can only be received by one of the other two sound heads. However, since the sound heads are arranged in the polygon, each oscillator body consists of an angular plate which, on being energised, emits sound signals in two different directions. In this way, it is possible to use a single oscillator body for the transmission and for the signals emitted by this oscillator body in different directions to be received by two sound heads. As an alternative, however, there is also the possibility of switching, for reception purposes, only that oscillator body which receives the signal of the one leg of the energised oscillator body, so that, of all angular oscillator bodies, always one is switched for transmission and at least one other is switched for reception. In this way, what happens is a cyclically rotating measurement of the lengths of the three measurement distances, approximately in the manner of a multiplex method.

In accordance with a second variant of the invention, provision is made for all sound heads to be constructed for the transmission and the reception of ultrasonic waves, and for each sound head to contain one oscillator body as transmitting oscillator and one oscillator body as receiving oscillator, the transmitting oscillator being disposed with its oscillating surface facing the oscillating surface of the receiving oscillator of another sound head.

In this case, each sound head contains two sound units which are separated functionally and electrically from one another and which are at an angle to one another as regards their arrangement in space. Using such an arrangement, it is possible, in principle, for the lengths of all measurement paths to be measured simultaneously, because all oscillator bodies can be operated independently of one another and, in each case, two oscillator bodies which are arranged in different sound heads form a measuring path as transmitter and receiver.

With both variants of the invention, the sound heads transmit strictly directed or bunched ultrasonic impulses, which are received by another sound head. In each case, the sound heads contain two oscillatable legs, which form either a single oscillator body or two oscillator bodies which functionally are separate from one another. Each of the legs is arranged with its oscillating surface facing a leg of another sound head. Various possibilities exist as regards the spatial arrangement of the two legs. According to a preferred constructional form of the invention, the vertices of the oscillator bodies formed by the legs are facing the part of the body. The consequence of this is that the ultrasonic waves which are generated by the two legs are transmitted in diverging directions, without intersecting one another along their path to the other sound head. Consequently, it is also possible for several length measurements by ultrasonics to be conducted simultaneously.

According to another constructional form of the invention, provision is made for the vertices formed by the oscillator bodies to be turned away from the part of the body, and for the length measurements of the measurement paths formed between the sound heads to be carried out in at least two successive measuring phases, thereby avoiding overlapping of sound waves. In this way, the decoupling is achieved by the measurements being carried out at different times. Although the paths of the ultrasonic signals intersect one another, the signals are not disputed.

BRIEF DESCRIPTION OF THE DRAWINGS

Two constructional example of the invention are hereinafter more fully explained, by reference to the drawings, wherein.

DESCRIPTION OF PREFERRED EMBODIMENTS

Figure 1:
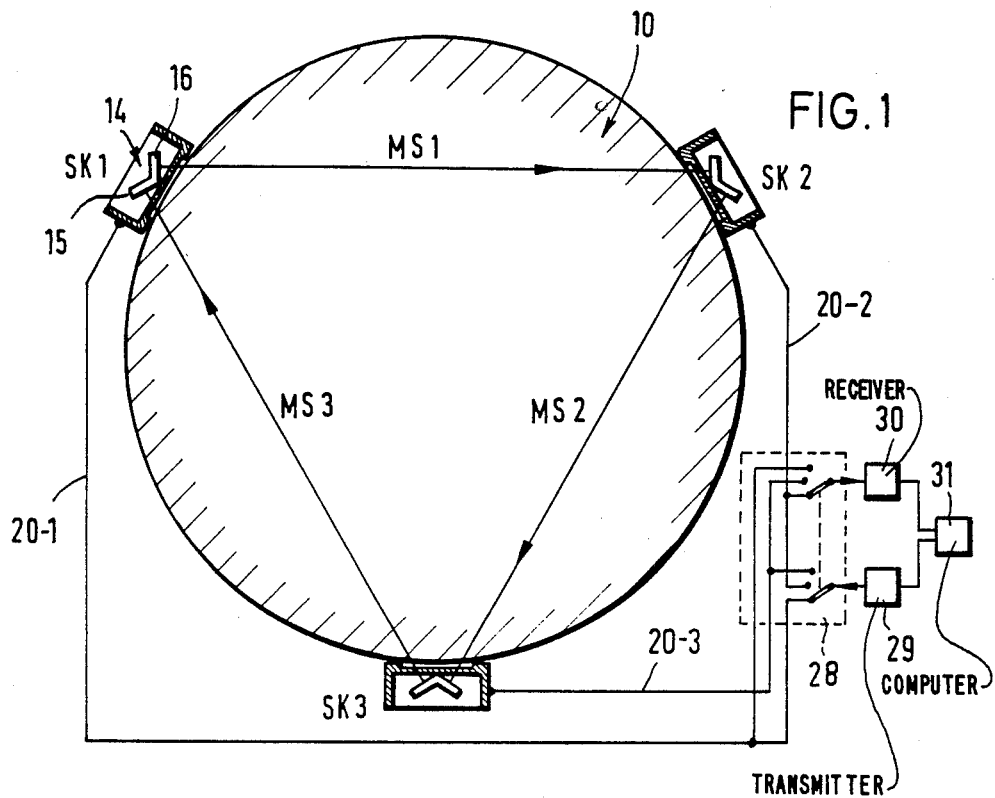
FIG. 1 is a diagrammatic view of the first constructional example.

Represented at 10 in FIG. 1 is the cross-section of a limb of a human or animal body. What is concerned is, for example, a cross-section of an extremity (arm or leg) which is not circular.

Arranged distributed around the limb 10 are three sound heads SK1, SK2, SK3. Each of the sound heads SK1 to SK3 can be reciprocally operated as an ultrasonic transmitter and ultrasonic receiver. For determining the length of the distance to be measured (MS1) between the sound heads SK1 and SK2, the sound head SK1 is operated as transmitter, while the sound head SK2 is operated as receiver. For measuring the length of the distance MS2 between the sound heads SK2 and SK3, the sound head SK2 is operated as transmitter, while the sound head SK3 is operated as receiver. For measuring the length of the distance MS3 between the sound heads SK3 and SK1, the sound head SK3 is operated as transmitter and the sound head SK1 as receiver. The measurements of these three distances MS1 to MS3 are carried out successively.

Figure 2:
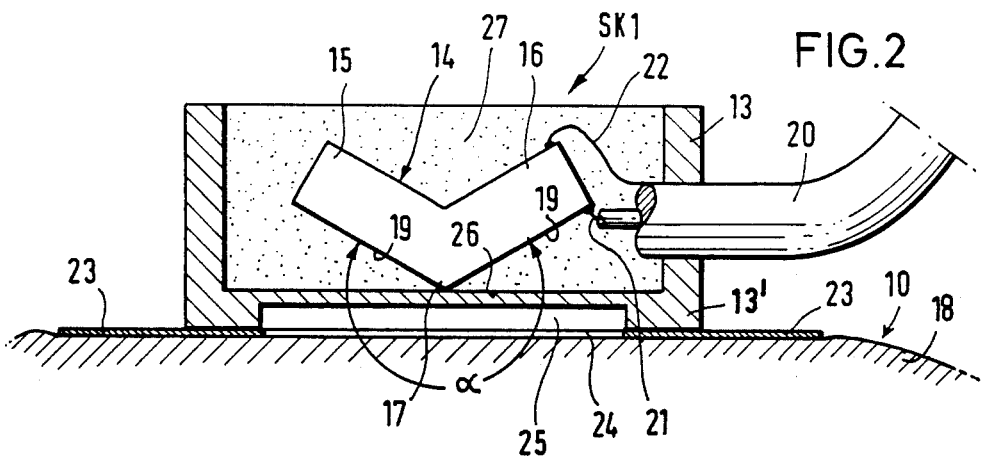
FIG. 2 is a longitudinal section through a sound head, which is used in the constructional example of FIG. 1.

Shown in FIG. 2 is a section through the sound head SK1. The sound heads SK2 and SK3 are constructed in like manner. Arranged in a port-shaped housing 13 of a synthetic plastics material, e.g. polyvinyl chloride, is an oscillator member 14 of piezoelectric ceramic material. The said member 14 consists of two legs 15, 16 which extend at an obtuse angle relatively to one another and which merge into one another to form a one-piece member. The vertex 17 of the oscillator member 14 is facing the body part 10 or the skin 18, against which the sound head 14 is placed. The oscillator member 14 is so arranged that the axis of symmetry or respectively the angle bisector passing through the vertex extends at right-angles to the surface of the skin 18. The oscillating or vibrating surfaces 19 of the legs 15 and 16 facing the part 10 of the body form an angle $\alpha$ of 240°. This means that the angle enclosed by the rearward surfaces of the legs 15 and 16 amounts to 120°.

A coaxial cable 20 leads into the housing 13, which cable is connected by its core 21 to the oscillating surfaces 19 and by its shielding 22 to the rear side of the oscillator member 14. Electric vibrations can be transmitted through the coaxial cable 20 to the piezoelectric oscillator member 14, whereby these oscillations are converted into ultrasonic waves, which are radiated by the oscillating surfaces 19. On the other hand, if one of the oscillating surfaces 19 receives an ultrasonic signal, this is converted in the oscillator member 14 into electric signals, which are conducted by way of the coaxial cable 20 to a receiver.

In the housing 13, the oscillator member 14 is embedded in a hardened adhesive 27, which fills the interior of the housing 13. The housing 13 is supported by a rim 13' on an adhesive ring 23, which consists of paper and is provided on both sides with an adhesive coating. The adhesive ring 23 is stuck by its underside on to the skin 18 and firmly secures the housing thereon. The adhesive ring 23 has a central opening 24, by which the chamber 25 enclosed by the bottom rim 13' of the housing 13 is connected to the surface of the skin 18. The chamber 25 contains a coupling gel, by which the ultrasonic signals are conducted in a particularly satisfactory manner. The chamber 25 is limited by the bottom wall 26 of the housing. The vertex 17 of the oscillating surface 19 of the oscillator member 14 bears against the bottom wall 26.

The coaxial cables 20, which lead to the individual sound heads SK1 to SK3, are respectively indicated in FIG. 1 by 20-1, 20-2 and 20-3. These cables lead to a switch unit 28 which, for reasons of simplicity, is represented as a mechanical switch unit, but which in practice is an electronic switch arrangement. In the switch unit 28, the individual wires are so connected to the electric transmitter device 29 and the receiver device 30 that respectively one of the sound heads is operated as a transmitter and another sound head as receiver. In this way, the distances MS1 to MS3 are successively measured. The evaluation of the signals of the transmitter unit 29 and of the receiver unit 30 takes place in a control device 31 or respectively in a computer. Furthermore, the surface area of the triangle is determined from the three measured distances MS1, MS2 and MS3 in the computer. The cross-sectional size of the part 10 of the body can then be determined from this surface area.

Figure 3:
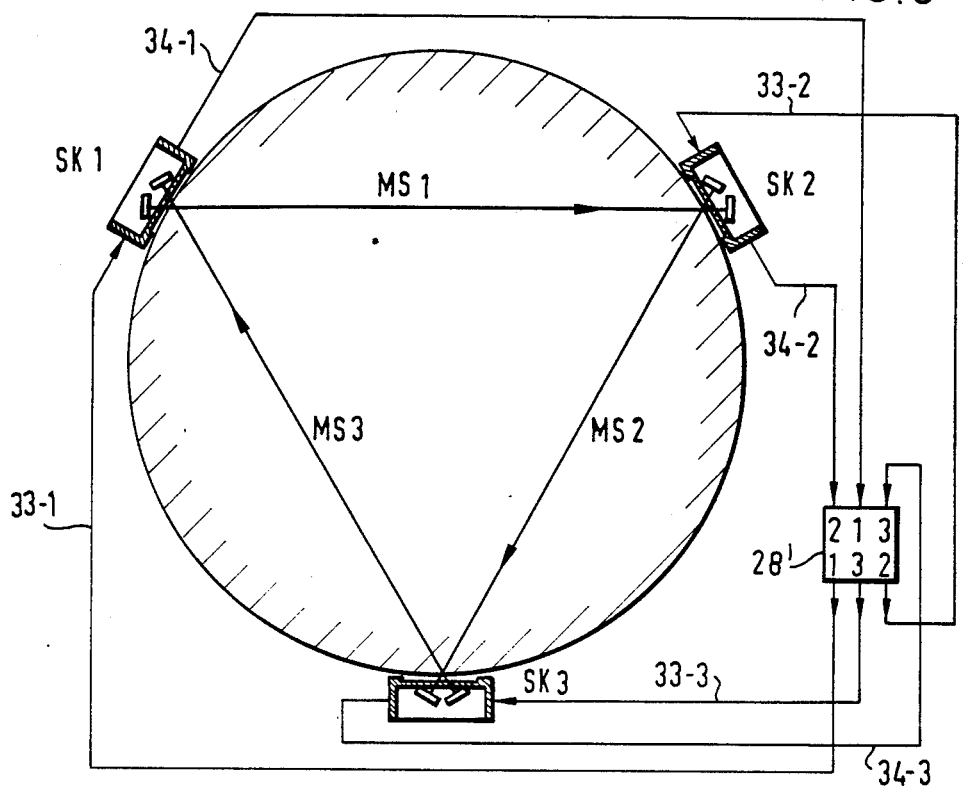
FIG. 3 is a diagrammatic view of the second constructional example.
Figure 4:
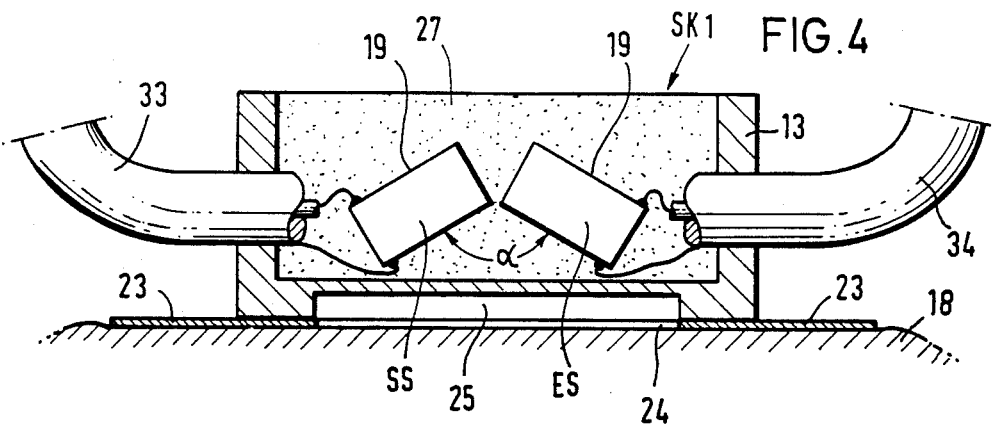
FIG. 4 is a longitudinal section through one of the sound heads, which are used in the second constructional example.

In the constructional example which is shown in FIGS. 3 and 4, the sound heads SK1 to SK3 each contain two oscillator members which are independent of one another and of which one is a transmitter oscillator SS and the other a receiver oscillator ES. The oscillator members enclose an angle $\alpha$ of 120° and the oscillating surfaces 19 thereof are facing the skin 18. The two oscillator members SS and ES are electrically and mechanically uncoupled from one another.

The transmitter oscillator SS is connected to a coaxial cable 33, which supplies the energiser signal to it, and the receiver oscillator ES is connected to a line 34, which carries the receiver signal. In FIG. 3, the lines which feed the electric transmission signal to the sound heads SK1 to SK3 are respectively indicated by 33-1 to 33-3, and the lines which carry the received signal from the associated oscillator member ES are indicated by 34-1 to 34-3. In the switching unit 28', to which all lines 33-1 to 33-3 and 34-1 to 34-3 are led, the controlling is so effected that the sound head SK2 receives when the sound head SK1 is transmitting, the sound head SK1 receives when the sound head SK3 is transmitting and the sound head SK3 receives when the sound head SK2 is transmitting. These three measuring phases take place in timed succession, which is controlled by the switch unit 28'.

It is to be further seen from FIG. 3 that the measuring distance or section MS1 first of all crosses the measuring section MS3 and then the measuring section MS2. This is because the oscillating surfaces 19 enclose an angle $\alpha$ of less than 180°, so that the measuring sections intersect one another.

With the arrangement according to the invention, the sound heads do not have to be connected to one another by a band, although a band may be additionally used, if necessary. It is sufficient to arrange the sound heads distributed at individual positions, to carry out the length measurements and thereafter to calculate the required area.

Instead of the arrangement with three sound heads, as shown, it is also possible to provide more than three sound heads, which are arranged distributed over the periphery of the part of the body and form the corner points of a polygon. If four sound heads are used, then with the measurement principle of FIGS. 1 and 2, the angle $\alpha$ is not 270°, but approximately 240°, and with the measurement principle of FIGS. 3 and 4, the angle $\alpha$ is not 120°, but approximately 90°. What is achieved in this way is that in each case two oscillating surfaces of oscillator members, which are arranged in adjacent sound heads, are facing one another. The larger the number of the sound heads being used, the more accurate is the measurement of the area, because the polygon is then better adapted to the contour of the part of the body.

The invention is not limited to measurements of cross-sections on parts of the human or animal body, but it also relates to measurements of the cross-section or of changes in cross-section on other objects, made of metal, synthetic plastics, wood or other materials.

We claim:

1. Apparatus for measuring cross-sections of objects comprising at least three sound heads which are adapted to be positioned about the periphery of an object whose cross-section is to be determined, each sound head includes oscillator means for selectively transmitting and receiving ultrasonic waves, said sound heads setting-off a polygon defined by the distance set-off between each pair of sound heads, computer means for transforming ultrasonic waves received from said oscillator means reflective of the distance between each pair of sound heads into the crosssection of an associated object, each said oscillator means includes a pair of angularly disposed legs each having an oscillating surface, each leg of each pair of legs of one sound head is positioned facing one other leg of one other pair of legs of another sound head, and switching means between said sound heads and said computer means for switching over said sound heads between transmission and reception to establish all distances set-off between each pair of sound heads whereby the ultrasonic waves received from said oscillator means are thereby transferred into the cross-section of an associated object.

2. The apparatus as defined in claim 1 wherein the polygon set-off by the sound heads is a triangle and the distance set-off between each pair of sound heads is one side of the triangle.

3. The apparatus as defined in claim 2 wherein said switching means is operative for transmitting ultrasonic waves received by the sound heads successively to said computer means.

4. The apparatus as defined in claim 2 wherein one leg of each oscillator means transmits ultrasonic waves and the other leg of each oscillator means receives ultrasonic waves.

5. The apparatus as defined in claim 2 wherein said switching means is operative for transmitting ultrasonic waves successively and sequentially from one sound head to the next.

6. The apparatus as defined in claim 2 wherein said switching means is operative for transmitting ultrasonic waves successively and sequentially from one sound head to the next, and transmitting the utrasonic waves successively and sequentially to said computer means.

7. The apparatus as defined in claim 2 wherein each pair of legs are joined by a vertex, and each vertex faces the periphery of the object whose cross-section is to be determined.

8. The apparatus as defined in claim 2 wherein each pair of legs define a vertex, and each vertex faces away from the periphery of the object whose cross-section is to be determined.

9. The apparatus as defined in claim 2 wherein the angle set-off between the oscillating surfaces of each pair of legs is approximately between 240° to 270°.

10. The apparatus as defined in claim 2 wherein the angle set-off between the oscillating surfaces of each pair of legs is approximately between 120° to 90°.

11. The apparatus as defined in claim 2 wherein each sound head includes a synthetic plastic housing, and adhesive means for securing each pair of legs in an associated housing.

12. The apparatus as defined in claim 2 wherein each sound head includes a housing having a chamber housing a coupling gel.

13. The apparatus as defined in claim 1 wherein said switching means is operative for transmitting ultrasonic waves received by the sound heads successively to said computer means.

14. The apparatus as defined in claim 13 wherein each pair of legs are joined by a vertex, and each vertex faces the periphery of the object whose cross-section is to be determined.

15. The apparatus as defined in claim 13 wherein each pair of legs define a vertex, and each vertex faces away from the periphery of the object whose cross-section is to be determined.

16. The apparatus as defined in claim 13 wherein the angle set-off between the oscillating surfaces of each pair of legs is approximately between 240° to 270°.

17. The apparatus as defined in claim 13 wherein the angle set-off between the oscillating surfaces of each pair of legs is approximately between 120° to 90°.

18. The apparatus as defined in claim 13 wherein each sound head includes a synthetic plastic housing, and adhesive means for securing each pair of legs in an associated housing.

19. The apparatus as defined in claim 13 wherein each sound head includes a housing having a chamber housing a coupling gel.

20. The apparatus as defined in claim 1 wherein one leg of each oscillator means transmits ultrasonic waves and the other leg of each oscillator means receives ultrasonic waves.

21. The apparatus as defined in claim 20 wherein each pair of legs define a vertex, and each vertex faces away from the periphery of the object whose cross-section is to be determined.

22. The apparatus as defined in claim 20 wherein the angle set-off between the oscillating surfaces of each pair of legs is approximately between 240° to 270°.

23. The apparatus as defined in claim 20 wherein the angle set-off between the oscillating surfaces of each pair of legs is approximately between 120° to 90°.

24. The apparatus as defined in claim 20 wherein each sound head includes a synthetic plastic housing, and adhesive means for securing each pair of legs in an associated housing.

25. The apparatus as defined in claim 20 wherein each sound head includes a housing having a chamber housing a coupling gel.

26. The apparatus as defined in claim 1 wherein said switching means is operative for transmitting ultrasonic waves successively and sequentially from one sound head to the next.

27. The apparatus as defined in claim 1 wherein said switching means is operative for transmitting ultrasonic waves successively and sequentially from one sound head to the next, and transmitting the ultrasonic waves successively and sequentially to said computer means.

28. The apparatus as defined in claim 1 wherein each pair of legs are joined by a vertex, and each vertex faces the periphery of the object whose cross-section is to be determined.

29. The apparatus as defined in claim 28 wherein the angle set-off between the oscillating surfaces of each pair of legs is approximately between 240° to 270°.

30. The apparatus as defined in claim 1 wherein each pair of legs define a vertex, and each vertex faces away from the periphery of the object whose cross-section is to be determined.

31. The apparatus as defined in claim 30 wherein the angle set-off between the oscillating surfaces of each pair of legs is approximately between 120° to 90°.

32. The apparatus as defined in claim 1 wherein the angle set-off between the oscillating surfaces of each pair of legs is approximately between 240° to 270°.

33. The apparatus as defined in claim 1 wherein the angle set-off between the oscillating surfaces of each pair of legs is approximately between 120° to 90°.

34. The apparatus as defined in claim 1 wherein each sound head includes a synthetic plastic housing, and adhesive means for securing each pair of legs in an associated housing.

35. The apparatus as defined in claim 1 wherein each sound head includes a housing having a chamber housing a coupling gel.

* * * * *